Figure 1:
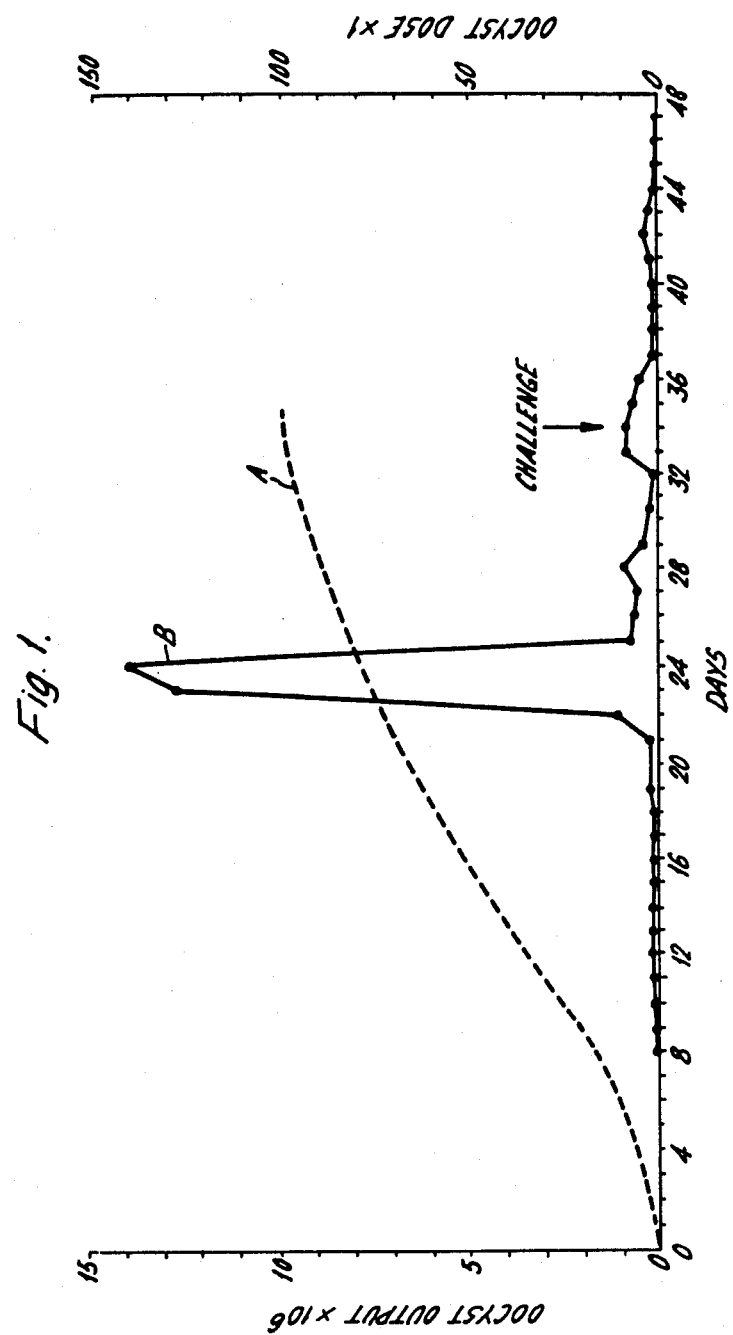

United States Patent [19]

Davis et al.

[11] Patent Number: 4,752,475

[45] Date of Patent: * Jun. 21, 1988

[54] COMPOSITIONS FOR THE CONTROL OF COCCIDIOSIS IN POULTRY

[75] Inventors: Paul J. Davis; James F. Reynolds, both of Bedfordshire, England

[73] Assignee: Unilever Patent Holdings B.V., Netherlands

[*] Notice: The portion of the term of this patent subsequent to Nov. 12, 2002 has been disclaimed.

[21] Appl. No.: 751,276

[22] Filed: Jul. 2, 1985

Related U.S. Application Data

[60] Division of Ser. No. 487,593, Apr. 27, 1983, Pat. No. 4,544,548, which is a division of Ser. No. 339,311, Jan. 15, 1982, abandoned, which is a division of Ser. No. 228,479, Jan. 26, 1981, abandoned, which is a continuation of Ser. No. 49,070, Jun. 18, 1979, abandoned, which is a continuation of Ser. No. 959,984, Nov. 13, 1978, abandoned.

[30] Foreign Application Priority Data

Nov. 14, 1977 [GB] United Kingdom ............. 047335/77

[51] Int. Cl.$^4$ ............................................. A61K 37/00
[52] U.S. Cl. ..................................................... 424/93
[58] Field of Search .......................................... 424/93

[56] References Cited

U.S. PATENT DOCUMENTS

| | | | |
|---|---|---|---|
| 3,857,971 | 12/1974 | Abdo et al. | 424/93 |
| 4,112,069 | 9/1978 | Huber | 424/93 |
| 4,138,498 | 2/1979 | Das | 424/93 |
| 4,544,548 | 10/1985 | Davis et al. | 424/93 |
| 4,552,759 | 11/1985 | Davis et al. | 424/93 |

OTHER PUBLICATIONS

"The Effect of Age of Bird and Degree of Exposure in the Development of Immunity to Cecal Coccidiosis in Chicks", Gordeuk et al, *Poultry Science*, pp. 503–508 (1951).

Joyner et al–Parasitology, vol. 72 (1976), pp. 115–125.

*Primary Examiner*—Sam Rosen
*Attorney, Agent, or Firm*—Kramer, Brufsky & Cifelli

[57] ABSTRACT

Essentially solid free-flowing pre-mixes and aqueous concentrates intended for addition to nutrient material in the manufacture of feedstuffs for poultry are provided consisting essentially of from about 1000 to about 1,000,000 viable sporulated oocysts of at least one species of coccidia to which poultry are susceptible and at least one edible thickening agent.

4 Claims, 2 Drawing Sheets

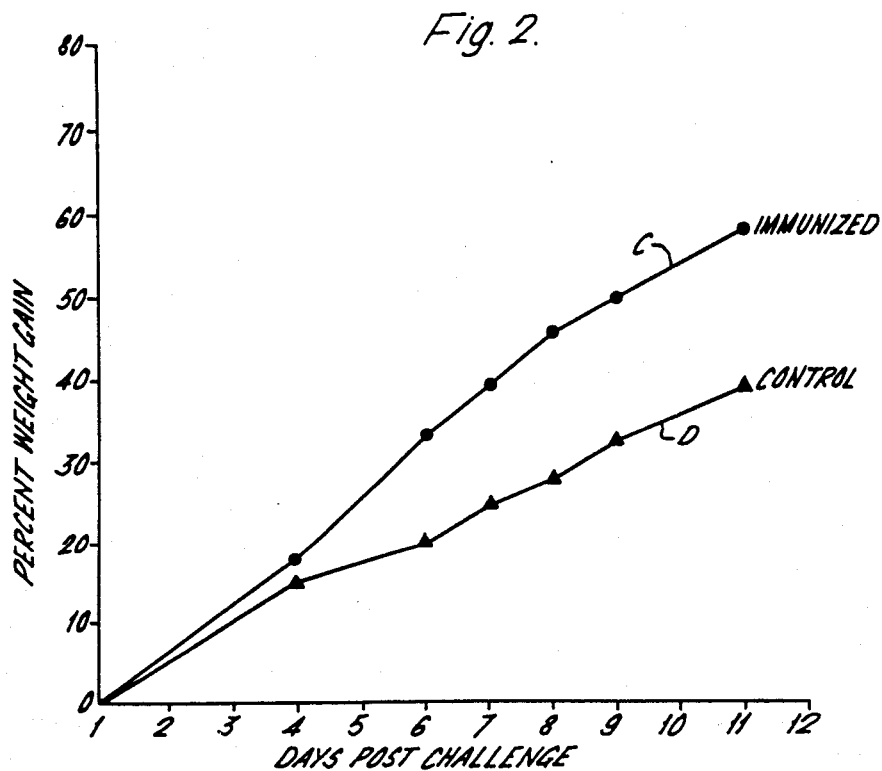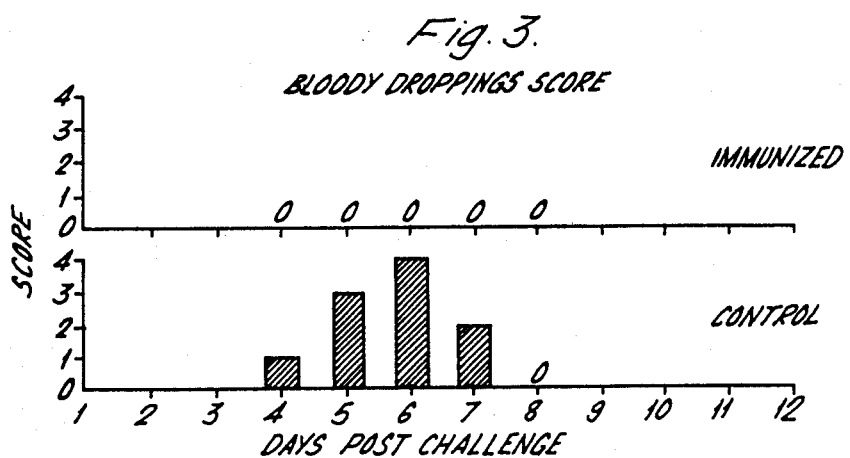

COMPOSITIONS FOR THE CONTROL OF COCCIDIOSIS IN POULTRY

CROSS-REFERENCE TO RELATED APPLICATIONS

This application is a division of application Ser. No. 487,593 filed on Apr. 27, 1983, now U.S. Pat. 4,544,548 which is a division of application Ser. No. 339,311 filed on Jan. 15, 1982, which was a division of application Ser. No. 228,479 filed on Jan. 26, 1981, which was a continuation of application Ser. No. 049,070 filed on June 18, 1979, which itself was a continuation of application Ser. No. 959,984 filed on Nov. 13, 1978, the latter four applications now abandoned.

The present invention relates to methods and compositions for the control of coccidiosis in poultry.

In this specification, the term "poultry" is used to denote birds of the order Galliformes such as the ordinary domestic fowl or chicken (*Gallus domesticus*), turkeys (Meleagris), pheasants (Phasianus), partridges (Perdix), grouse (Lagopus), guinea fowl (Numida) and peacocks (Pavo), and also birds of the order Anseriformes such as ducks (Anas) and geese (Anser).

Coccidial infections are encountered in all poultry species that are reared by man. Such infections are particularly troublesome when they occur in flocks of birds reared under modern intensive husbandry conditions. Infection can spread rapidly throughout the flock, and at the very least can cause poor growth. Severe infection can lead to death of the birds. Thus for many years considerable effort has been expended in attempts to find reliable prophylactic measures against such infections, and in particular to find ways in which birds can be immunised effectively against the incidence of such infections. The practical benefit of any effective immunising technique will be to promote the growth of poultry to which immunity is imparted, at least in the sense that the negative effects on growth caused by coccidial infection will be counteracted thereby.

It has already been established that poultry which have survived infection by coccidiosis retain some degree of immunity against further infection. This effect has been put to practical use in a procedure described in U.S. Pat. No. 3,147,186 wherein sub-clinical infection is induced in poultry by the administration of a single oral inoculum containing 100–800 viable sporulated coccidia oocysts per bird. The resulting infection, re-inforced by secondary and tertiary cycles of infection caused when the birds pick up further viable sporulated oocysts resulting from those excreted by infected birds, imparts immunity to the flock as a whole. The efficiency of this technique is enhanced if an anti-coccidial drug is administered to the poultry at a sub-curative level, so reducing the pathogenic effects of the coccidia while still permitting the life cycle of the organism to produce further viable sporulated oocysts in the litter which can be ingested by other members of the flock. An oral liquid inoculum of viable sporulated coccidia oocysts for this purpose is available commercially. While this is undoubtedly an effective technique for imparting immunity to poultry, it requires the poultry farmer to conduct a specific inoculating procedure over and above all of the normal tasks that need to be performed in conventional poultry rearing. Moreover, in unskilled hands, there is the risk that in error a dangerous overdose of oocysts could be administered to the birds, leading to severe and perhaps fatal infection. Finally, conditions of temperature and moisture in the litter must be carefully controlled to ensure the sporulation of excreted oocysts necessary to induce the progressive cycles of immunising infection. One embodiment of the procedure described in U.S. Pat. No. 3,147,186 is the administration of the single oral inoculum of oocysts via the drinking water or the feedstuff given to the poultry. Nevertheless, neither of these variants overcomes the problems of the additional task imposed on the poultry farmer or the possible risk of overdose, as it still remains the responsibility of the farmer to prepare the inoculated water or feedstuff and to administer it at the correct time. A further disadvantage acknowledged in U.S. Pat. No. 3,147,186 in relation to administration of the single inoculum via a specially prepared feedstuff is that it is best to wait until the poultry have learned to eat before presenting them with the inoculated feedstuff. Thus by implication the dangerous post-hatching period during which the chicks have no immunity against coccidial infection could be prolonged unduly through delayed administration of the inoculum.

Thus we believe there is still a need for a method of imparting immunity to poultry which does not impose any additional tasks or responsibilities on the poultry farmer and which reduces the potential risk of overdose.

By the invention it has been found that poultry can be immunised effectively against coccidiosis if a low level of viable sporulated oocysts of one or more coccidia species infective to the species of poultry concerned is administered in a feedstuff given to the poultry on a continuous or at least frequent basis.

Accordingly, the invention firstly provides a method for promoting the growth of poultry, in which method the poultry are reared on a diet comprising nutrient feed material containing added viable sporulated oocysts of at least one species of coccidia to which the poultry are susceptible, the oocysts being present in a concentration sufficient only to induce sub-clinical infection in the poultry.

To this end, another embodiment of the invention is a commercial poultry feedstuff comprising nutrient material and containing per kg thereof from about 10 to about 10,000 viable sporulated oocysts of at least one coccidia species to which poultry are susceptible.

By providing the poultry with oocysts in their regular feedstuff, the poultry are able in effect to conduct a controlled progressive self-inoculation. Daily intake of oocysts is dictated by the quantity of feedstuff eaten by each bird, and the level of oocysts in the feedstuff can be regulated by the feedstuff manufacturer whose sophisticated quality control facilities can more readily ensure that no risk of overdose can possible arise. Moreover, by having the oocysts in their normal diet, it is possible to ensure that the chicks are consuming appropriate levels of oocysts as soon as they begin to ingest solid food, and thus the immunising process can begin at a very early moment in their post-hatching life.

Different species of poultry suffer from infections caused by different coccidia species. The domestic fowl (*Gallus domesticus*) can be infected by any of the coccidia *Eimeria tenella, E. necatrix, E. brunetti, E. maxima, E. acervulina* and *E. praecox*. The following coccidia are implicated in infections of turkeys (Meleagris): *Eimeria melagrimitis, E. dispersa, E. meleagridis, E. gallopavonis, E. adenoides, E. innocua* and *E. subrotunda*. Domestic ducks (Anas) suffer from infections caused by

*Tyzzeria perniciosa* and also, it is believed by *Eimeria anatis* which they can acquire from wild ducks (*Anas platyrhyncos*). Geece (Anser) can suffer from infections caused by *Eimeria anseris, E. nocens* and *E. parvula*, and in addition it is believed that domestic geese can pick up infections from Canada geese caused by *Eimeria hermani, E. striata* and *E. fulva*. The other poultry species referred to earlier each suffer from infections caused by characteristic coccidia, and the invention is equally appropriate and effective in the control of infections caused by the characteristic coccidia in such other poultry species. All oocysts levels mentioned in this specification should be construed as being per each coccidia species present.

Preferably the poultry feedstuff of the invention will contain not more than about 2,500 viable sporulated oocysts per kg. Although positive benefits will be obtained by the introduction of the sporulated oocysts into the feedstuff given to an individual bird at any stage of its life, it is preferable that the bird is provided with a feedstuff containing the low levels of sporulated oocysts as soon as it has been hatched and commences feeding. As the bird grows, its daily food requirement increases dramatically. Taking the domestic fowl (*Gallus domesticus*) as an example, at the "first feeding" stage the chick will consume approximately 2g of feedstuff per day. After 10 days this will have risen to about 10 g per day, and after 30 days the bird will be consuming perhaps 80 g per day. The nutritional requirements of the bird change as it develops, and commercially-available poultry feedstuffs are sold with a range of formulations intended for the different stages of the bird's development. Typically such a range will include feedstuffs specifically formulated for "starters", "growers" and "breeders/layers". In order to ensure that at each stage of its development the bird is consuming an appropriate number of sporulated coccidia oocysts per day, it may be appropriate for the different feedstuffs to contain different numbers of oocysts per kg.

For optimum immunization, we believe that a newly-hatched chick should consume about 1 to 20 viable sporulated oocysts per day. During the first 10 days of growth, this level should rise to about 2 to 50 oocysts per day. By day 30, the level of oocysts consumed per day should be of the order of about 5 to 200.

Preferably a "starter" feedstuff will contain at least about 500 viable sporulated oocysts per kg. Preferably the maximum level of oocysts will be about 5,000 per kg, and ideally not more than about 2,000 per kg.

In a "grower" feedstuff the minimum level of viable sporulated oocysts is preferably about 50 per kg. The upper level of oocysts is preferably about 2,000 per kg, and ideally not more than about 500 per kg.

In a "breeder/layer" feedstuff an appropriate minimum level of viable sporulated oocysts is about 10 per kg. Preferably the upper level of oocysts does not exceed about 1,000 per kg, and ideally is not greater than about 100 per kg.

The viable sporulated oocysts can be obtained by deliberately infecting a donor flock of birds, and collecting the oocysts from their droppings. Techniques for obtaining viable sporulated coccidia oocysts per se are well known in the art, and form no part of the present invention. One suitable procedure is described at length in U.S. Pat. No. 3,147,186.

The oocysts can be added directly during the mixing of the poultry feedstuff, or can be added via a pre-mix. Alternatively, a suspension of the oocysts, preferably aqueous, can be sprayed onto the poultry feedstuff. This is particularly useful when a pelleted feedstuff is required, because the oocysts must not be applied until all steps involving heat in the manufacture of the feedstuff have been completed. The oocysts are very easily killed by heat, and a procedure such as pelleting would destroy any oocysts present in the pelleted mixture. Due to the heat-sensitivity of the oocysts, a feedstuff of the invention must not be exposed to any extremes of heat during storage. Moreover, the oocysts are also damaged if they suffer dehydration, and for this reason the feedstuff should never be allowed to dry out completely. Preferably the moisture level in the feedstuff should remain in the range of about 6 to about 12% by weight, although higher moisture levels can be used where this does not lead to spoilage of the feedstuff by the growth of moulds, etc, during storage.

A further embodiment of the invention is an essentially solid free-flowing pre-mix comprising viable sporulated coccidia oocysts distributed in a carrier, which can be added as a dry composition to a poultry feedstuff formulation, or which can be made into a paste or slurry with water for incorporation into a poultry feedstuff by admixture or by spraying. Preferably the carrier is an edible thickening agent, such as a colloid-forming material although materials that form gels can also be employed. One suitable thickening agent is a starch, such as potato starch, wheat starch or maize (corn) starch. However, starches suffer from the disadvantage that they are not so readily mixable with water, and can lead to relatively lumpy pastes. A more preferred thickening agent is a cold water soluble polysaccharide, such as an alkyl cellulose, a carboxyalkyl cellulose or a hydroxyalkyl cellulose. Sodium carboxymethyl cellulose is especially preferred. Alternatively, gums such as locust bean gum, guar gum and gum tragacanth can be used. If desired, mixtures of any of these thickening agents can be employed. The number of sporulated oocysts incorporated in the pre-mix will depend on the number required per unit weight of the poultry feedstuff and the desired or permitted level of the carrier in the poultry feedstuff. Typically, a pre-mix of the invention will include at least 1,000 sporulated oocysts per kg. Preferably this minimum level will be at least about 5,000 per kg, and ideally at least 10,000 per kg. A typical general-purpose pre-mix can contain from about 50,000 to about 500,000 sporulated oocysts per kg. A maximum level is not readily definable: a pre-mix containing in excess of one million sporulated oocysts per kg could be useful where a high oocyst level in the feedstuff is needed but where the carrier level must be kept to a minimum. It will be appreciated that pre-mixes of type just described can be used also to aid the incorporation of other essential trace ingredients into the poultry feedstuff, for example, mineral additives which are important especially in promoting egg-shell formation in laying birds, vitamins and amino acids such as lysine, and carotenoid pigments commonly used to influence the colour of egg yolks. If desired, one or more of these minor ingredients can be included with the oocysts together in one composite pre-mix. To maintain the viability of the oocysts, the pre-mix should have a moisture content in the preferred range of about 6 to about 12% by weight.

Another embodiment of the invention is an aqueous concentrate containing viable sporulated oocysts, intended for addition as such during the manufacture of poultry feedstuffs. Like the essentially solid pre-mix just described, such an aqueous concentrate can be an article of commerce in its own right. Preferably the aqueous concentrate contains the oocysts in suspension. To this end, it is preferable that the aqueous concentrate also comprises one or more edible thickening agents of the types just described in relation to the essentially solid pre-mix. The same preferences for cold water soluble polysaccharides in general, and sodium carboxymethylcellulose in particular, apply. In this instance, however, only low levels of such materials, sufficient to promote the suspending ability of the aqueous concentrate without so increasing its viscosity that it becomes unpourable or unsprayable (depending on the desired mode of addition to the poultry feedstuff) are required. Very broadly, it can be said that the optimum level for any given thickening agent is likely to lie in the range of about 0.1 to about 10% by weight of the aqueous concentrate, but it will be appreciated that the properties of commercially available thickening agents vary widely one from another. The levels of oocysts in the aqueous concentrate are governed by the same considerations as those just described in relation to the essentially solid pre-mix: thus strictly comparable levels are appropriate. An advantage of an aqueous oocyst concentrate containing an edible thickening agent such as a cold water soluble polysaccharide is that the thickening agent binds water. When the aqueous concentrate is blended with dry ingredients in the manufacture of a poultry feedstuff the binding of the water by the thickening agent prevents rapid absorption of the water into the feedstuff and thus assists in the spreading of the oocysts uniformly throughout the bulk of the feedstuff. If the water is absorbed too rapidly, the resulting local concentrations of oocysts may be difficult to break up by subsequent processing without undue risk of loss of viability due to frictional heat, for example.

Due to the loss of viability that can result if the sporulated oocysts are allowed to dehydrate, it can be advantageous to encapsulate the oocysts within a relatively water-impervious edible material. Clearly the encapsulating material should be such that release of the oocysts within the gut of the bird is effected readily. Optimally the encapsulating material should have a melting point at or slightly below the body temperature of the bird, which is typically about 40° C. However, materials of higher melting point can be used so long as the resulting capsule is sufficiently fragile to be crushed in the gizzard of the bird. It will be appreciated that where the encapsulating material is to be applied in the molten state, the temperature and heat transfer characteristics of the encapsulation procedure must not be such that the sensitive oocysts suffer a significant loss of viability due to being overheated. In practice it is preferable that the melting point of the encapsulating material should be in the range of about 35° to about 60° C. Fats and waxes, such as stearine, having melting points within this range are particularly suitable. An appropriate encapsulating technique is co-extrusion of the molten encapsulating material around an aqueous suspension of the oocysts, using for example the well-known 3M process. The aqueous suspension preferably comprises the oocysts in physiological saline or phosphate-buffered saline.

Apart from the inclusion therein of the viable sporulated oocysts, it is not essential for the composition or physical form of the poultry feedstuff to be altered in any way in putting the invention into effect. Any of the currently standard "complete" or nutritionally "balanced" commercial poultry feedstuff formulations can be used, and the nutrient material in the feedstuff can thus comprise any of the protein, carbohydrate and fat ingredients normally found in such feedstuffs. The nature of such standard ingredients, such as the various fish meals, milled grain and other plant material, and mineral additives, and the nutritional requirements such as minimum levels of vitamins, amino acids and trace elements, are well known in the art and documented in the technical literature, and such detail forms no part of the present invention.

The treatment and prevention of coccidial infections in poultry using anti-coccidial drugs is well known. However, in an important preferred sub-feature of the invention we have found that very effective control of coccidial infections can be achieved if in addition to feeding the poultry with a feedstuff containing sporulated coccidia oocysts in accordance with the invention, the poultry are also exposed to one or more anti-coccidial drugs at a curative level. We have observed that this combination of sporulated oocysts in the feed and the additional administration of anti-coccidial drug interrupts the life cycle of the parasite and effectively prevents any transmission of infective oocysts throughout the entire course of immunisation. In this respect the present invention represents a further departure from the concepts disclosed in U.S. Pat. No. 3,147,186, wherein an anti-coccidial drug is used at a sub-curative level merely to reduce the pathogenic effects of the coccidia without eliminating their ability to produce the viable sporulated oocysts needed to induce further cycles of sub-clinical immunising infection. In our invention we prefer the anti-coccidial drug to halt effectively the life cycle of the coccidia, so preventing excretion of viable oocysts into the environment. Thus, in the ideal situation, the birds would ingest only those oocysts which have been deliberately added to their diet. Clearly, the anti-coccidial drug used in accordance with our invention must not be one which halts the coccidia life cycle at so early a stage that no development takes place in the gut of the bird sufficient to induce an appropriate immune response.

Preferably the anti-coccidial drug used is one in which the major activity is directed against parasitic stages of the coccidium appearing on the fourth day of infection or later. Examples of appropriate anti-coccidial drugs are nicarbazin, furazolidone, nitrofurazone, nihydrazone, sulphaquinoxalene, sulphanitran, dinsed, ormetroprim, sulphadimethoxine and ethopabate. The anti-coccidial drug can be included as an ingredient of the feedstuff itself, or if preferred it can be administered separately to the poultry. Standard curative dose rates as recommended by the manufacturer of the drug can be employed.

The invention will now be described, by way of example only, with reference to the control of infections in the domestic fowl (*Gallus domesticus*) caused by *Eimeria tenella*, which is one of the least immunogenic of all coccidial species, and certainly one of the most pathogenic and virulent. Any technique that is demonstrably effective in the control of *Eimeria tenella* infections will, by implication, be at least equally effective against the less intractable coccidia.

The accompanying drawings, of which:

FIG. 1 is a graph illustrating the numbers of oocysts ingested and excreted by birds fed an immunising diet of the invention;

FIG. 2 is a graph comparing the percent weight gain of two groups of birds following a severe challenge with viable coccidia oocysts, one group of birds having been immunised in accordance with the invention; and FIG. 3 is a pair of block diagrams illustrating in terms of excreted bloody droppings the symptoms exhibited by the two groups of birds whose percent weight gain is compared in FIG. 2; are relevant to Example 1.

EXAMPLE 1

(1) Management of Birds

Newly hatched Cobb broiler chicks were collected from a commercial hatchery and immediately divided at random into groups of six. Groups in which the oocyst output was to be monitored were kept in cages having an open wire-mesh floor through which their droppings could fall, and those which were intended to demonstrate the efficacy of the oocyst-containing feedstuff were kept on litter. The accommodation in which all chicks were housed had been thoroughly treated to ensure freedom from residual oocysts.

(2) Oocysts

Oocysts were obtained by infecting 3-week old Cobb broiler chicks by an oral dose of 5,000 oocysts per bird. Their droppings were collected on days 6, 7 and 8 after infection, mixed with approximately twice their volume of 2.5% aqueous potassium dichromate solution and then homogenised to give a smooth slurry. The slurry was strained through a nylon gauze and the oocysts were recovered from the filtrate by salt floatation, as follows. Firstly, the oocysts were sedimented by centrifugation at 1,000 x g for 15 minutes and the sediment was then resuspended in saturated aqueous sodium chloride solution. This was subjected to centrigugation at 500 x g for 10 minutes, and the oocyst suspension which remained was drawn off and diluted with 10 volumes of distilled water. Centrifugation at 1,000 x g for 15 minutes brought the oocysts down into a pellet. The whole salt floatation procedure was repeated, and the resulting oocyst pellet was finally taken up in 2.5% aqueous potassium dichromate. The extracted oocysts were sporulated by continuous aeration of this suspension for four days at 28° C. As a stock suspension, these oocysts were maintained at 4° C. in phosphate bufffered saline.

(3) Preparation of the oocysts-containing feed

Birds were immunized by a continuous "trickle" of low numbers of oocysts given in the feed. They were added at a level of 1,250 per kg. of meal. To ensure even spreading throughout the whole feed and to provide an additional means of mechanical protection, the oocysts were first suspended in a starch paste which was then mixed with the meal in a Hobart cutter/mixer bowl. The paste was prepared by making a smooth, thick suspension of 300 g of wheat flour with 1,000 ml of cold water. The paste was steamed for 30 minutes and then cooled before addition of the oocysts, at a level of 6,000 per 125 ml of paste. This provided enough material to treat 4,500 g of meal. Birds were fed ad-libatum on this feed and their oocyst intake was calculated from the amount of feed consumed. Line A in FIG. 1 gives the number of oocysts consumed by each bird per day of the experiment up to day 34.

(4) Viability of Oocysts

The viability of the oocysts in the feed was checked at fortnightly intervals by feeding the diet to fresh susceptible birds and then monitoring their oocyst output on days 6-11 after the start of oocyst feeding.

(5) Assessment of Infections

The effects of the immunizing infections were monitored by the daily rate of oocyst discharge (average per bird), the rate of weight gain and the presence of blood in the droppings. Line B in FIG. 1 shows the average daily oocyst output of each bird consuming the oocyst-containing feed. Weights were recorded at weekly intervals during the immunization period but more frequently after the challenge. They were expressed as the percentage weight increase since the start of the immunization or since the administration of the challenge inocula. Lines C and D in FIG. 2 show respectively the average percentage weight gain of the immunized and control birds after challenge.

When blood was seen in the droppings, a crude assessment was made on the basis of the number of fresh blood-containing droppings which could be seen. A scoring range of 0-4 was used, from 0 (absent) through 2 (frequent) to 4 (uniformly scattered). The results obtained are recorded in FIG. 3.

(6) Continuous In-Feed Immunization

This experiment was designed to established whether sporulated oocysts added to the feed in very low numbers could survive and cause controlled, sub-clinical infections when fed to susceptible birds. The immunity arising from this treatment, continued for 34 days, was tested by means of a severe challenge with 500,000 oocysts. Three groups, each of six birds, were used. The first and second groups received the oocyst-containing diet from one day old and the third received a normal, oocyst-free diet. In order to simulate the least favourable conditions likely to be encountered in commercial situations, groups 1 and 3 were kept on deep litter. Group 2 was kept on wire so that the daily oocyst discharge resulting from the oocysts in the diet could easily be monitored.

(7) Results

The oocysts survived in the feed for the duration of the experiment, as oocysts were passed from day 8 right up to the time that the immunizing diet was withdrawn, as shown in FIG. 1. Also, when the diet was fed to fresh susceptible birds, large numbers of oocysts were passed on days 6-11 following dosing. It was obvious from the pattern of oocyst discharge that a substantial immunity was beginning to develop soon after the birds reached 3 weeks of age, for a soaring oocyst discharge was promptly checked and brought under control by day 25, despite the continual intake of oocysts at an increasing rate. Challenge on day 34 with 500,000 oocysts produced only a trival peak of oocyst discharge on day 42.

The immunizing oocysts produced no detectable pathogenic effects, despite the fact that these birds were on litter and could have picked up numerous fresh oocysts. No bloody droppings were seen throughout the whole immunizing period but, more importantly, the mean weight gains of the control, unimmunized group and the immunized group were statistically identical up to the day of challenge.

Challenge with 500,000 oocysts on day 34 caused severe disease in the control group as can be seen from the statistically significant differences in weight gain and the bloody droppings score shown in FIGS. 2 and 3. The immunized group were apparently completely unaffected but there was no mortality in either group.

(8) Conclusions

The most important conclusions to be drawn from these results are that oocysts added to the diet in this way survive for at least one month and that, administered in this form, they can induce a strong immunity without causing pathogenic effects. Despite the use of fully virulent organisms the unique, self-limiting nature of the coccidial life cycle can be exploited, allowing complete control to be exercised over the level of infection and its consequent pathogenicity during the critical phases of immunization.

Clearly, the fresh oocysts discharged into the litter did not constitute a hazard. The conditions under which the birds were kept were designed to allow the maximum opportunity for re-infection, but because each bird was receiving a steady dose of oocysts in its feed, and effective, if not solid, immunity had built up before extensive sporulation could occur.

Because the oocysts were included in the feed they would have been taken in constantly, rather than at daily vaccinating events and the process of vaccination was, in effect, carried out by the birds themselves without the need for any additional handling. An inevitable consequence of this mode of administration would be that the birds would receive a steadily increasing dose of oocysts as their food intake increased. When a bird consumed 10 g of food in one day, then the daily oocyst dose would have been about 10, increasing to about 50 when the bird's food consumption increased to 50 g per day. An equally important feature was that once the oocysts had been uniformly distributed throughout the meal, there could be no possibility of an overdose—the bulk of food which would have been necessary to provide a dangerous number of oocysts was excessive.

The control birds were seriously affected by the challenge, but overall, they fared better than expected. This was almost certainly due to failure to completely exclude oocysts from their environment and, since the conditions in which they were kept were not designed to prevent infection, it is possible that they may have acquired some slight resistance.

Nevertheless, by the time the oocyst-containing feed was withdrawn at day 34, the immunized birds were completely in equilibrium with their environment and were capable of withstanding a massive infection of oocysts.

EXAMPLE 2

An aqueous concentrate was prepared by taking up approximately 6,000 viable sporulated *Eimeria tenella* oocysts, obtained in the manner described in Example 1, in 100 ml physiological saline (0.85% by weight sodium chloride in water) containing dissolved therein 2.5 g sodium carboxymethyl cellulose (Hercules KLUCEL). This concentrate was blended with 4,500 g of a standard commercial poultry meal, using a Hobart cutter-mixer the concentrate simply being poured into the bowl of the rotating mixer containing the meal, mixing being continued until a visually homogeneous product resulted. Domestic fowl reared from hatching on this feedstuff exhibited the same good immunity against *E. tenella* challenge as was exhibited by the immunized chicks of Example 1.

What is claimed is:

1. An essentially solid free-flowing pre-mix, intended to be mixed with nutrient material in the manufacture of a feedstuff for poultry, consisting essentially of at least one edible thickening agent in which are distributed, per kilogram of pre-mix, from about 1000 to about 1,000,000 viable sporulated oocysts of at least one species of coccidia to which poultry are susceptible, said pre-mix containing from about 6 to about 12 percent by weight moisture.

2. A pre-mix as claimed in claim 1, wherein said edible thickening agent is sodium carboxymethyl cellulose.

3. A pre-mix as claimed in claim 1 wherein the edible thickening agent is selected from the group consisting of starches, cold water soluble polysaccharides, gums, and mixtures thereof.

4. A pre-mix as claimed in claim 1 wherein said pre-mix additionally contains trace ingredients selected from the group consisting of minerals, vitamins, amino acids, carotenoid pigments, and mixtures thereof.

* * * * *